United States Patent
Hattori et al.

(10) Patent No.: US 6,632,458 B1
(45) Date of Patent: Oct. 14, 2003

(54) FOOD USING γ-AMINOBUTYRIC ACID-ENRICHED CRUCIFEROUS PLANT

(75) Inventors: Toshimitsu Hattori, Fukuoka (JP); Shinji Tsusaki, Fukuoka (JP); Kinya Takagaki, Fukuoka (JP)

(73) Assignee: Toyo Shinyaku Co., Ltd. (JP)

( * ) Notice: Subject to any disclaimer, the term of this patent is extended or adjusted under 35 U.S.C. 154(b) by 0 days.

(21) Appl. No.: 09/654,325

(22) Filed: Sep. 1, 2000

(30) Foreign Application Priority Data

Sep. 2, 1999 (JP) .......................................... 11-249166
Jun. 23, 2000 (JP) ...................................... 2000-189561
Jun. 23, 2000 (JP) ...................................... 2000-189562
Jun. 23, 2000 (JP) ...................................... 2000-189563

(51) Int. Cl.[7] .......................... A61K 35/78; A61K 9/00; A61K 47/00; A23K 1/165
(52) U.S. Cl. ...................... 424/725; 424/400; 424/439; 424/442
(58) Field of Search ................ 424/725, 400, 424/439, 442

(56) References Cited

FOREIGN PATENT DOCUMENTS

| JP | 53-56350 | | 5/1978 |
|---|---|---|---|
| JP | DW 1985-078043 | * | 2/1985 |
| JP | 3-236763 | | 10/1991 |
| JP | 6-169689 | * | 6/1994 |
| JP | 8-173111 | | 7/1996 |
| JP | 9-205989 | | 8/1997 |
| JP | 10-42841 | | 2/1998 |

* cited by examiner

Primary Examiner—Christopher R. Tate
Assistant Examiner—Randall Winston
(74) Attorney, Agent, or Firm—Webb Ziesenheim Logsdon Orkin & Hanson, P.C.

(57) ABSTRACT

A cruciferous plant, cut pieces thereof, and juice of the plant and the cut pieces are subjected to at least one treatment selected from the group consisting of anaerobic treatment, 25 to 50° C. thermal retention treatment, and glutamic acid treatment, to enrich γ-aminobutyric acid (GABA), thereby obtaining a cruciferous plant, cut pieces, and juice containing GABA in various concentrations. By performing microwave radiation, blanching, drying, and the like for the GABA-enriched plant and the like as required, dried powder of the cruciferous plant, the cut pieces, and the juice, containing GABA in a high concentration and maintaining green color, is obtained. Food material, medicine material, and feed made of the cruciferous plant containing GABA in a high concentration are obtained.

1 Claim, No Drawings

FOOD USING γ-AMINOBUTYRIC ACID-ENRICHED CRUCIFEROUS PLANT

BACKGROUND OF THE INVENTION

1. Field of the Invention

The present invention relates to cruciferous plants rich in γ-aminobutyric acid (hereinafter, abbreviated as GABA). More particularly, the present invention relates to cruciferous plants, cut pieces of the plants, juice of the plants and cut pieces, and dried powder of the plants, the cut pieces, and the juice that maintains green color and has a high GABA content, a method for producing the same, and foods, beverages, and medicine materials made of the same.

2. Description of the Related Art

Since GABA has a hypotensive function, studies have been made for producing foods containing a large amount of GABA for those suffering from hypertension. For example, "gabalong" tea is known where picked tea-leaves are left in an anaerobic atmosphere during a tea production process to allow a large amount of GABA to be accumulated in the tea-leaves. Japanese Laid-Open Patent Publication No.8-173111 describes production of coffee leaves having a high GABA concentration. Specifically, coffee leaves are left in an anoxic atmosphere, then heat-treated at a high temperature of 110° C. or more, and dried. Japanese Laid-Open Patent Publication No. 9-205989 describes increasing the GABA content in tea-leaves by irradiating the tea-leaves with infrared.

The tea-leaves obtained in the above conventional methods are of the type of pouring boiling water to the tea-leaves to extract ingredients thereof. Therefore, only effective ingredients that are soluble in water are ingestible.

Cruciferous plants such as kale contain a large amount of vitamins and the like and thus have received attention for their usability as health food. Juice and dried powder have already been produced from a cruciferous plant such as kale to be used for beverages and foods. In order to maintain the green color of a cruciferous plant, as well as dried powder and juice produced therefrom, blanching is performed where a cruciferous plant is subjected to high-temperature treatment using extremely hot water or the like. However, effective ingredients of the cruciferous plant tend to be lost during this hot-water treatment. This method therefore fails to provide a processed cruciferous plant that keeps effective ingredients from being lost while maintaining the green color.

For example, Japanese Laid-Open Patent Publication No. 10-42841 describes a method for producing juice from a cruciferous plant. In this method, a cruciferous plant (e.g., cabbage) is shredded, and vitamin C is added thereto. The resultant cabbage shredded pieces are heat-treated and then squeezed to produce juice. According to this method, however, nutrients in the plant that are sensitive to heat are disadvantageously decomposed during the heat treatment.

Japanese Patent Gazette No.2796227 describes a method for producing dried powder from a cruciferous plant. In this method, the plant is treated at a comparatively low temperature by combining 12 to 13 hour preliminary drying and far infrared radiation. This method still has a shortcoming that only nutrients inherently possessed by a cruciferous plant such as kale are provided for ingestion. If a nutrient or a medicinal ingredient (e.g., GABA) can be additionally included in the cruciferous plant, it will be possible to ingest the effective ingredient (e.g., GABA) in a large amount directly, not through extraction as described above. Such a cruciferous plant will provide an additional effect as health food.

In consideration of the above, desired are dried powder, juice, and dried powder of juice of a cruciferous plant that contain an additional nutrient or medicinal ingredient.

SUMMARY OF THE INVENTION

As a result of vigorous study on cruciferous plants, the present inventors have found that cruciferous plants contain GABA, an ingredient having a hypotensive function, and succeeded in increasing the GABA content in cruciferous plants. The present invention is based on this success. Cruciferous plants are especially suitable as objects subjected to treatments for increasing the GABA content, and thus GABA-enriched cruciferous plants have been successfully obtained.

The present invention provides a GABA-enriched cruciferous plant, which is edible as it is. The GABA-enriched cruciferous plant may be dried, to provide dried powder containing a large amount of GABA. The GABA-enriched cruciferous plant may also be squeezed, to provide juice containing an abundance of GABA. Further, by drying the juice, dried powder of juice containing an abundance of GABA is provided. Thus, there is provided health food having a new effect of hypotensive function in addition to the conventional effects of juice and dried powder of a cruciferous plant.

The present invention provides a cruciferous plant, cut pieces of the plant, or juice of the plant or the cut pieces, containing GABA in an amount of 50 mg/100 g or more.

In a preferred embodiment, the cruciferous plant, the cut pieces of the plant, or the juice of the plant or the cut pieces maintains a green color.

The present invention further provides a cruciferous plant, cut pieces of the plant, or juice of the plant or the cut pieces, containing GABA in an amount of 10 mg/100 g or more, which are blanched and maintain a green color.

The present invention provides a method for producing a cruciferous plant or cut pieces of the plant containing GABA in an amount of 50 mg/100 g or more, wherein the method comprises enriching GABA in a cruciferous plant or cut pieces of the plant, wherein enriching GABA includes at least one treatment selected from the group consisting of anaerobic treatment, 25 to 50° C. thermal retention treatment, and glutamic acid treatment.

In a preferred embodiment, the method further comprises microwave treatment.

In a yet preferred embodiment, the cruciferous plant or the cut pieces of the plant is subjected to the treatment to maintain a green color.

The present invention also provides a method for producing juice of a cruciferous plant containing GABA in an amount of 50 mg/100 g or more, wherein the method comprises: enriching GABA in a cruciferous plant or cut pieces of the plant; and squeezing the enriched cruciferous plant or cut pieces of the plant, wherein enriching GABA includes at least one treatment selected from the group consisting of anaerobic treatment, 25 to 50° C. thermal retention treatment, and glutamic acid treatment.

Further, the present invention provides a method for producing juice of a cruciferous plant containing GABA in an amount of 50 mg/100 g or more, wherein the method comprises enriching GABA in the juice of a cruciferous plant or cut pieces of the plant, wherein enriching GABA includes at least one treatment selected from the group consisting of anaerobic treatment, 25 to 50° C. thermal retention treatment, and glutamic acid treatment.

In a preferred embodiment, the method further comprises microwave treatment.

In a more preferred embodiment, the treated juice maintains a green color.

The present invention provides a dried powder of a cruciferous plant or cut pieces of the plant containing GABA in an amount of 180 mg/100 g or more.

The present invention further provides a method for producing dried powder of a cruciferous plant or cut pieces of the plant containing GABA in an amount of 180 mg/100 g or more, wherein the method comprises: enriching GABA in a cruciferous plant or cut pieces of the plant; and drying the enriched cruciferous plant or cut pieces of the plant, wherein enriching GABA includes at least one treatment selected from the group consisting of anaerobic treatment, 25 to 50° C. thermal retention treatment, and glutamic acid treatment.

The present invention also provides dried powder of a cruciferous plant or cut pieces of the plant, containing GABA in an amount of 10 mg/100 g or more and maintaining a green color.

In a preferred embodiment, the dried powder further contains vitamin B1 in an amount of 0.1 mg/100 g or more and vitamin C in an amount of 100 mg/100 g or more.

Furthermore, the present invention provides a method for producing dried powder of a cruciferous plant or cut pieces of the plant containing GABA in an amount of 10 mg/100 g or more and maintaining a green color, wherein the method comprises: performing microwave treatment on a cruciferous plant or cut pieces of the plant; and drying the treated cruciferous plant or cut pieces of the plant.

In a preferred embodiment, the method further comprises subjecting at least one treatment selected from the group consisting of anaerobic treatment, 25 to 50° C. thermal retention treatment, and glutamic acid treatment.

Yet, the present invention provides a method for producing dried powder of a cruciferous plant or cut pieces of the plant containing GABA in an amount of 10 mg/100 g or more and maintaining a green color, wherein the method comprises: enriching GABA in a cruciferous plant or cut pieces of the plant; blanching the enriched cruciferous plant or cut pieces of the plant; and drying the blanched cruciferous plant or cut pieces of the plant, wherein enriching GABA includes at least one treatment selected from the group consisting of anaerobic treatment, 25 to 50° C. thermal retention treatment, and glutamic acid treatment.

The present invention also provides a dried powder of juice of a cruciferous plant containing GABA in an amount of 350 mg/100 g or more.

The present invention provides a method for producing dried powder from juice of a cruciferous plant containing GABA in an amount of 350 mg/100 g or more, wherein the method comprises: enriching GABA in a cruciferous plant or cut pieces of the plant; squeezing the enriched cruciferous plant or cut pieces of the plant; and drying the resultant juice, wherein enriching GABA includes at least one treatment selected from the group consisting of anaerobic treatment, 25 to 50° C. thermal retention treatment, and glutamic acid treatment.

The present invention also provides dried powder of juice of a cruciferous plant containing GABA in an amount of 10 mg/100 g or more and maintaining a green color.

In a preferred embodiment, the dried powder further contains vitamin B1 in an amount of 0.1 mg/100 g or more and vitamin C in an amount of 100 mg/100 g or more.

The present invention also provides a method for producing dried powder from juice of a cruciferous plant containing GABA in an amount of 10 mg/100 g or more and maintaining a green color, wherein the method comprises: performing microwave treatment on a cruciferous plant; squeezing the treated cruciferous plant; and drying the resultant juice.

The present invention further provides a method for producing dried powder from juice of a cruciferous plant containing GABA in an amount of 10 mg/100 g or more and maintaining a green color, wherein the method comprises: performing microwave treatment for juice of a cruciferous plant; and drying the treated juice.

The present invention also provides a method for producing dried powder from juice of a cruciferous plant containing GABA in an amount of 10 mg/100 g or more and maintaining a green color, wherein the method comprises: enriching the GABA in a cruciferous plant or cut pieces of the plant; blanching the enriched cruciferous plant or cut pieces of the plant; squeezing the blanched cruciferous plant or cut pieces of the plant; and drying the resultant juice, wherein enriching the GABA includes at least one treatment selected from the group consisting of anaerobic treatment, 25 to 50° C. thermal retention treatment, and glutamic acid treatment.

The present invention provides a method for producing dried powder from juice of a cruciferous plant containing GABA in an amount of 10 mg/100 g or more and maintaining a green color, wherein the method comprises: enriching the GABA in the juice of a cruciferous plant or cut pieces of the plant; blanching the enriched juice of the cruciferous plant or the cut pieces of the plant; and drying the blanched juice, wherein enriching the GABA includes at least one treatment selected from the group consisting of anaerobic treatment, 25 to 50° C. thermal retention treatment, and glutamic acid treatment.

Further, the present invention provides a method for producing a cruciferous plant or cut pieces of the plant having an increased content of GABA, wherein the method comprises subjecting a cruciferous plant or cut pieces of the plant to at least one treatment selected from the group consisting of anaerobic treatment, 25 to 50° C. thermal retention treatment, and glutamic acid treatment.

Moreover, the present invention provides a method for producing dried powder of a cruciferous plant or cut pieces of the plant having an increased content of GABA, wherein the method comprises: drying the cruciferous plant or the cut pieces of the plant obtained by the above-mentioned method; and powdering the dried cruciferous plant or cut pieces of the plant.

Further, the present invention provides a method for producing a juice from a cruciferous plant having an increased content of GABA, wherein the method comprises performing on the juice of a cruciferous plant or cut pieces of the plant at least one treatment selected from the group consisting of anaerobic treatment, 25 to 50° C. thermal retention treatment, and glutamic acid treatment.

The present invention also provides a method for producing a juice from a cruciferous plant having an increased content of GABA, wherein the method comprises: performing on a cruciferous plant or cut pieces of the plant at least one treatment selected from the group consisting of anaerobic treatment, 25 to 50° C. thermal retention treatment, and glutamic acid treatment; and squeezing the treated cruciferous plant or cut pieces of the plant.

Moreover, the present invention provides a method for producing a dried powder from juice of a cruciferous plant having an increased content of GABA, wherein the method comprises: drying the juice of the cruciferous plant or the cut pieces of the plant obtained by the above mentioned method; and powdering the dried juice of the cruciferous plant or the cut pieces of the plant.

Furthermore, the present invention provides a method for producing a dried product of cut pieces of a cruciferous plant having an increased content of GABA, wherein the method comprises: performing on a cruciferous plant at least one treatment selected from the group consisting of anaerobic treatment, 25 to 50° C. thermal retention treatment, and glutamic acid treatment; cutting the treated cruciferous plant into cut pieces; and drying the cut pieces.

The present invention relates to a method for maintaining a green color of a cruciferous plant, cut pieces of the plant, a juice from the plant or the cut pieces, or a dried powder of the plant, the cut pieces, or the juice, comprising performing microwave treatment on the cruciferous plant, the cut pieces of the plant, or the juice of the plant or the cut pieces.

Moreover, the present invention provides a food, beverage, or medicine material containing at least one substance selected from the group consisting of:

a cruciferous plant, cut pieces of the plant, or juice of the plant or the cut pieces containing GABA in an amount of 50 mg/100 g or more;

a cruciferous plant, cut pieces of the plant, or the juice of the plant or the cut pieces containing GABA in an amount of 50 mg/100 g or more and maintaining a green color;

a cruciferous plant, cut pieces of the plant, or the juice of the plant or the cut pieces containing GABA in an amount of 10 mg/100 g or more and blanched to maintain a green color;

a dried powder of a cruciferous plant, cut pieces of the plant, or juice of the plant or the cut pieces containing GABA in an amount of 180 mg/100 g or more; and a dried powder of a cruciferous plant, cut pieces of the plant, or juice of the plant or the cut pieces containing GABA in an amount of 10 mg/100 g or more and maintaining a green color.

In a preferred embodiment, the cruciferous plant is kale.

DETAILED DESCRIPTION OF THE INVENTION

Examples of cruciferous plants include cabbage, broccoli, cauliflower, kale, radish, horseradish, and Komatsuma (a kind of Chinese cabbage). Among these, kale is most preferable. Note that the "cruciferous plant" as used herein does not necessarily refer to the entire plant, but may sometimes refer to part of the plant such as a leaf or a stem.

According to the present invention, cut pieces of a cruciferous plant are also used. Cutting of a cruciferous plant into pieces may be performed by a method generally used for cutting plants into pieces by those skilled in the art, such as slicing, crushing, and shredding. This also includes slurrying, which is performed with a juicer, a blender, a mass-colloider, or the like. By slurrying, a cruciferous plant becomes porridgy (a suspension of solid particles in a liquid). A cruciferous plant may be cut into pieces so that 80% or more of the pieces have a mean diameter of 1 mm or less, preferably 0.5 mm or less, more preferably 0.1 mm or less, most preferably 0.05 mm, so as to be provided with flowability.

Note that the term "cruciferous plant" as used herein includes cut pieces of the cruciferous plant when cut pieces are not individually referred to. Note also that the term "juice" as used herein refers to juice of a cruciferous plant or cut pieces thereof unless otherwise specified.

Juice is obtained by squeezing a cruciferous plant and, as required, subjecting the cruciferous plant to a process normally performed by those skilled in the art, such as filtering and centrifuging. Juice may be prepared after water or a solution such as a buffer (including an isotonic sodium chloride solution) is added to the cruciferous plant as required. The juice as used herein includes, not only green juice obtained by squeezing a cruciferous plant, but also extract such as ethanol extract, warm to extremely hot water extract, land hydrous alcohol extract from the cruciferous plant, and ethanol extract from dried powder of the juice.

A cruciferous plant and juice therefrom are generally blanched for maintaining a green color thereof. According to the present invention, a cruciferous plant is first subjected to a treatment for increasing the GABA content (hereinafter, referred to as "GABA enriching treatment" or "GABA enrichment"). Then, blanching or an alternative treatment such as steaming and microwave radiation is performed. After being cooled as required, the plant is dried and pulverized or otherwise treated appropriately, to produce food materials, medicine materials, or feed.

Hereinafter, treatments of GABA enrichment, blanching, and microwave radiation will be described individually.

GABA Enrichment

GABA in a cruciferous plant can be enriched by performing for the cruciferous plant or juice thereof at least one treatment selected from the group consisting of anaerobic treatment, 25 to 50° C. thermal retention, and glutamic acid treatment.

Anaerobic Treatment and/or 25 to 50° C. Thermal Retention

The anaerobic treatment and the 25 to 50° C. thermal retention a re performed singularly or in combination for a cruciferous plant or juice thereof.

The anaerobic treatment refers to a treatment with a gas containing little oxygen or no oxygen at all, including a treatment in the vacuum state. As such a gas, carbon dioxide gas and nitrogen gas are preferably used. The treatment is performed while keeping the temperature preferably at 25 to 50° C., more preferably 30 to 45° C. for the time period of 10 minutes to 72 hours, preferably 3 to 24 hours.

For the thermal retention, any means may be used, including hot water, infrared radiation, warm air, an incubator, heating and insulation, and the like. Infrared radiation is preferably used.

In the infrared radiation treatment, a cruciferous plant may be directly irradiated with infrared using an appropriate infrared radiation apparatus. Alternatively, a cruciferous plant may be sealed before the irradiation with infrared, to prevent moisture in the plant from evaporating. For example, a cruciferous plant that has been sealed for prevention of moisture evaporation may be irradiated with infrared using an infrared radiation apparatus of 400W power to keep the temperature at 25 to 50° C., preferably 30 to 45° C. for 10 minutes to 24 hours, preferably 30 minutes to six hours.

Since the temperature rises during the infrared radiation, a temperature sensor may be placed inside, so that the radiation can be continued for an appropriate duration under control of the internal temperature to be kept constant (e.g., at 40° C.). A far infrared radiation apparatus may also be used.

In the heating and insulation treatment, a cruciferous plant in the sealed state is exposed to warm air of 25 to 50° C., preferably 30 to 45° C., and this temperature is kept for 10 minutes to 24 hours, preferably 30 minutes to six hours. In the hot water treatment, a cruciferous plant is exposed to hot water of 25 to 50° C., preferably 30 to 45° C., and this temperature is kept for 10 minutes to 24 hours, preferably 30 minutes to six hours.

The duration of the anaerobic treatment and/or the thermal retention is preferably 10 minutes to 24 hours, more preferably one to six hours. The temperature to be kept during the treatment is preferably about 25 to about 50° C., more preferably about 30 to about 45° C., most preferably around 40° C. If the temperature is less than 25° C. or exceeds 50° C., the GABA content is less likely to increase.

GABA can also be enriched by preserving or storing a cruciferous plant or juice thereof in an isothermal chamber kept at a constant temperature (e.g., 25 to 50° C.).

The anaerobic treatment and/or the thermal retention is preferably performed under the conditions where a cruciferous plant or juice thereof is prevented from drying.

As a result of the anaerobic treatment and/or the thermal retention, the GABA content in the cruciferous plant and the juice thereof increases. For example, as shown in Table 1 in Example 1 described later, the GABA content increases about 3.6 times for broccoli leaves, about six times for cabbage leaves, and about 6.2 times for kale leaves.

Glutamic Acid Treatment

The glutamic acid treatment as used herein refers to one of the following procedures: (1) immersing a cruciferous plant or cut pieces thereof in a solution including glutamic acid, salt thereof, or other food material containing glutamic acid or salt thereof (hereinafter, collectively called "glutamic acids"); (2) adding glutamic acids to cut pieces of a cruciferous plant; and (3) adding glutamic acids to juice of a cruciferous plant. The glutamic acid added to the cruciferous plant is changed to GABA by catalysis of enzymes existing on the surface and inside of the cruciferous plant, whereby the GABA content increases.

For a cruciferous plant in a non-liquid form, that is, the plant as it is or cut pieces thereof having a mean diameter more than 1 mm, the glutamic acid treatment is performed by immersing the plant or the cut pieces thereof in a solution containing glutamic acids (hereinafter, sometimes called an immersion solution). A buffering agent and the like generally used by those skilled in the art may be added to the immersion solution.

For a cruciferous plant in a liquid form, that is, cut pieces of the cruciferous plant having a mean diameter of 1 mm or less or juice thereof, the glutamic acid treatment is performed by adding glutamic acids to the cut pieces or juice of the cruciferous plant.

The concentration of the glutamic acid or salt thereof in the immersion solution or that to be added is not specifically limited but may be appropriately adjusted depending on the amount of GABA desired to be enriched. The immersion solution may be a saturated or supersaturated solution. The concentration of the glutamic acid or salt thereof is generally 0.01 to 40% (by weight; this is also applied to the subsequent percentages unless otherwise specified), preferably 0.2 to 20%, more preferably 0.5 to 10%.

Examples of the salt of glutamic acid include glutamates known to those skilled in the art, such as sodium glutamate, potassium glutamate, calcium glutamate, and magnesium glutamate. The glutamic acid or salt thereof may be added directly, or a solution containing glutamic acid or salt thereof in a high concentration may be added.

The other food material containing glutamic acid or salt thereof as used herein refers to any food materials containing glutamic acid or salt thereof other than the cruciferous plant used. Examples of such food materials include: seaweed such as sea tangle and wakame seaweed; mushrooms such as siitake mushrooms and maitake mushrooms; fish such as bonito (including dried bonito) and sardine; shells such as short-necked clams and corbicula; rice, wheat, and soybean (including germs thereof); and tea-leaves, mulberry leaves, Vegetables (e.g., tomato), citrus fruits (mesocarp, bags of endocarp). Among these, food materials containing glutamic acid or salt thereof in a comparatively high concentration are preferable. Food materials usable for the present invention also include those of which edible protein has been subjected to enzymatic treatment, heating, and the like to liberate or produce glutamic acid.

The food material as described above may be added to the immersion solution directly, or dried powder of the food material may be added, depending on the form of the food material. Alternatively, ingredients contained in the food material may be eluted in water, ethanol, or the like while heating as required, and the resultant solution or dried powder thereof may be added. Otherwise, a cruciferous plant may be immersed in the eluate. For example, when the glutamic acid-containing food material is dried sea tangle, water with dried sea tangle therein is heated to elute ingredients of the sea tangle. By using the resultant eluate (stock), GABA in the plant can be efficiently increased.

The temperature used for the glutamic acid treatment for GABA enrichment is not specifically limited, but preferably in the range of temperatures where the enzyme catalyzing the change of glutamic acid to GABA will not be inactivated. The temperature is therefore preferably 20 to 50° C., more preferably 25 to 45° C.

The pH used for the glutamic acid treatment may be appropriately adjusted for the purposes of facilitating the GABA enrichment and obtaining a final product having vivid green color. The pH adjustment is performed with a pH adjusting agent generally used by those skilled in the art. The pH is normally 3.5 to 9.0, preferably 4.0 to 8.0, more preferably 4.5 to 7.0. If the pH is adjusted toward an alkaline value, more vivid green color is obtained compared with the case of treating the plant with an acidic solution or performing no such treatment. If the pH is 3 or less, the efficiency of the GABA enrichment may sometimes decrease and the plant is browned. Therefore, treatment with pH 3 or less is not preferable.

The duration of the glutamic acid treatment for GABA enrichment is preferably 10 minutes to 24 hours. By continuing the treatment for 30 minutes or more, the GABA content dramatically increases.

The efficiency of the GABA enrichment will be further enhanced by combining the glutamic acid treatment with the anaerobic treatment and the thermal retention described above. More specifically, the anaerobic treatment can be incorporated in the glutamic acid treatment by directly introducing nitrogen into the immersion solution or a reaction solution by bubbling or the like, by replacing ambient gas, or by deaerating, for example. Also, the GABA enrichment can be facilitated by retaining an appropriate temperature.

The efficiency of the glutamic acid treatment for GABA enrichment will also be enhanced by adding an inorganic chloride such as pyridoxal phosphate and common salt and the like to the immersion solution. Examples of the inorganic chloride include sodium chloride (common salt), calcium chloride, potassium chloride, and magnesium chloride, which are known to those skilled in the art. Bittern, bay salt, and the like may also be used. Such an inorganic chloride may be added in an arbitrary concentration, but is generally added so that the final concentration is 0.01 to 20%, preferably 0.02 to 10%. For example, suppose 3% of sodium glutamate is added to 100 g (wet weight) of kale (pH 6.0) and the kale is left to stand at 30° C. for five hours. In this case, if sodium chloride is added so that the final concentration thereof is 0.5% by weight, the GABA content will increase by about three-tenths compared with the case of adding no sodium chloride.

Increase in GABA Content by GABA Enrichment

Raw leaves of a cruciferous plant intrinsically include GABA in an amount of about 30 mg/100 g (about 170 mg/100 g by dry weight). By the GABA enriching treatments described above, the amount of GABA can be increased to at least 180 mg/100 g, preferably 200 mg/100 g or more, more preferably 300 mg/100 g or more, further preferably 500 mg/100 g or more, further more preferably 1000 mg/100 g or more (all dry weight). The upper limit of the GABA amount is not defined, but the GABA amount of 3000 mg/100 g or more (dry weight) is possible by appropriately determining the concentration of the glutamic acid and the like, the treatment duration, and the temperature and pH of the solution, and using the microwave radiation, the infrared radiation, the anaerobic treatment, and the like described above singularly or in combination.

The GABA-enriched cruciferous plant is drained, and the resultant plant, as it is or after being cut into pieces, can be used as a food material, a medicine material, or feed. The GABA-enriched cruciferous plant or cut pieces thereof may be squeezed, and the resultant juice may be used as a food material, a medicine material, or feed. The GABA-enriched cruciferous plant, cut pieces thereof, or juice thereof may be dried to obtain dried products or dried powder.

Blanching

In general, therefore, in the processing of a cruciferous plant, juice thereof, and dried powder of the plant and the juice, high-temperature treatment called blanching is performed using extremely hot water, steam, or the like, for deactivating enzymes and the like involved in deterioration of the plant (fading of the green color and change in flavor).

Blanching includes high-temperature treatments using extremely hot water, steam, and the like generally performed by those skilled in the art. For example, an appropriate amount of a cruciferous plant (e.g., 10% by weight with respect to treatment water) is put in 95 to 100° C. hot water, left to stand for 30 seconds to five minutes, then immediately moved to 5° C. cold water, and immersed therein for an appropriate duration (e.g., about five minutes). During the blanching, sodium bicarbonate, sodium carbonate, and/or sodium chloride are added singularly or in combination in an appropriate amount. By this treatment, the green color is vividly maintained.

Such blanching reduces the GABA amount. However, as described above, it has been found that by performing the abovedescribed GABA enrichment prior to the blanching, a desired amount of GABA remains in the cruciferous plant although the GABA amount decreases. In other words, by combining the GABA enrichment and the blanching, obtained are a cruciferous plant and juice thereof having a GABA content significantly higher than those obtained by the conventional blanching.

Microwave Treatment

To overcome the problem of the blanching that GABA is lost, the present inventors have studied to find a treatment method replacing the conventional blanching, in which the GABA content will not be easily reduced. As a result, it has been found that microwave radiation is effective in maintaining the green color without reducing the GABA content. By adopting this treatment, the present inventors have succeeded in obtaining a cruciferous plant, juice thereof, and dried powder of the plant and the juice that maintain the green color and have an extremely high GABA content.

The microwave radiation is a moderate treatment compared with the blanching. The microwave radiation can suppress the decrease with time of the contents of effective ingredients such as GABA, vitamins (especially, water-soluble vitamins), minerals, chlorophyll, and the like, and also can suppress fading of the vivid green color and change in flavor.

If the microwave radiation is excessive, nutrients and effective ingredients such as GABA and vitamins contained in a cruciferous plant may be lost. The microwave radiation is therefore desirably limited to the range within which enzymes involved in color fading can be deactivated to maintain the green color and also effective ingredients are prevented from being lost due to excessive radiation. This range may be appropriately determined based on the power of the microwave radiation apparatus, the wavelength of the microwave used, the irradiation duration, and the kind and amount of the cruciferous plant.

For example, when 2450 MHz, 500 W microwave is used, 100 g (wet weight) of kale as the cruciferous plant may be irradiated for 0.5 to 10 minutes, preferably 0.5 to 5 minutes, more preferably 0.5 to 1 minute. If the duration is less than 0.5 minute, deactivation of enzymes is insufficient, resulting in easy fading. If the duration exceeds 10 minutes, effective ingredients tend to decrease. Even by this decrease, however, the resultant GABA content is very high compared with the case of blanching with extremely hot water, and the green color is maintained, as will be described later in the examples.

Since the enzymes involved in deterioration have been deactivated in the microwave-radiated cruciferous plant, ingredients contained therein can b e retained stably for a prolonged time period. Moreover, since vivid green color is maintained, the commercial value as health food or a material thereof is high.

Thus, by appropriately combining the GABA enrichment, the blanching, and the microwave radiation, provided are a cruciferous plant, cut pieces thereof, juice of the plant and the cut pieces that have a desired GABA content and maintain green color as desired.

Cooling

Cooling is performed as required after a cruciferous plant or juice thereof has been heated during the treatment such as GABA enrichment, microwave radiation, and blanching described above.

In cooling, the treated cruciferous plant or juice thereof is immersed in a water bath or an ice bath, chilled or frozen.

Since the enzymes involved in deterioration have been deactivated in the treated cruciferous plant or juice thereof, ingredients contained therein can be retained stably for a prolonged time period. Moreover, since vivid green color is maintained, the commercial value as health food or a material thereof is high.

Drying

The cruciferous plant or juice thereof subjected to GABA enrichment and blanching or microwave radiation as required as described above is then dried as required.

During drying of a cruciferous plant, moisture of the plant is reduced to 10% or less, preferably 5% or less. Drying is performed by a method generally used by those skilled in the art, including drying with hot air, warm air, far infrared, high-pressure steam, and electromagnetic wave, spray drying, and freeze drying. A drying method that does not increase the temperature so high is preferable in view of preservation of nutrients in the plant. Drying is preferably performed at a temperature as low as possible. If heated for drying, the temperature should be in the range of 50 to 80° C., for example, preferably in the range of 55 to 65° C. To prevent the green color from fading from the cruciferous plant or juice thereof during the drying, an alkaline aqueous solution may be applied to the cruciferous plant before the drying.

Cut pieces or juice of a cruciferous plant is preferably dried by spray drying or freeze drying. Further, during drying, an excipient and the like, such as dextrin, cyclodextrin, starch, and maltose, may be added.

Powdering

The dried product is further pulverized to obtain dried powder. Pulverization is made by a method generally employed by those skilled in the art. For example, the dried product is crushed with a crusher, a mill, a blender, a stone mill, or the like. The crushed pieces may be sifted as required, to obtain, for example, those that have passed through a sieve having a 30 to 250 mesh as the dried powder of a cruciferous plant. If the grain size of the crushed pieces is smaller than 250 mesh, handling may be difficult in further processing of the dried powder. If the grain size is larger than 30 mesh, uniform mixing with other food materials may be difficult.

By appropriately combining the GABA enrichment, the microwave radiation, and the blanching, and then performing cooling, drying, and pulverizing as required as described above, obtained are a GABA-enriched cruciferous plant, juice thereof, and dried powder of the plant and the juice having various GABA contents, that are described below in detail under the first through eighth inventions.

In the following description, the GABA content is expressed by wet weight in the case of the cruciferous plants, cut pieces thereof, and juice of the plants and the cut pieces, and by dry weight in the case of the dried powder. First invention: Cruciferous plant, cut pieces thereof, or juice of the plant or cut pieces containing GABA in an amount of 50 mg/100 g or more.

The cruciferous plant of the first invention is obtained by subjecting a cruciferous plant to GABA enrichment.

The cut pieces of the cruciferous plant of the first invention are obtained by first subjecting a cruciferous plant to GABA enrichment and then cutting the GABA-enriched cruciferous plant into pieces, or by first cutting a cruciferous plant into pieces and then subjecting the cut pieces to GABA enrichment.

In general, among the cruciferous plants, kale has a highest GABA content, which is about 30 mg/100 g. There have never existed such a cruciferous plant and cut pieces thereof having a GABA content as high as 50 mg/100 g or more as those of this invention, which are therefore novel.

The juice of the first invention is obtained by first subjecting a cruciferous plant or cut pieces thereof to GABA enrichment and then squeezing the GABA-enriched plant or cut pieces thereof to obtain juice, or first squeezing a cruciferous plant or cut pieces thereof to obtain juice and then subjecting the juice to GABA enrichment.

In general, among juice of the cruciferous plants, juice of kale has a highest GABA content, which is about 30 mg/100 g. There have never existed such a juice of cruciferous plant or cut pieces thereof having a GABA content as high as 50 mg/100 g or more as those of this invention, which are therefore novel. The GABA content of the juice of the GABA-enriched cruciferous plant or cut pieces thereof, in particular, GABA-enriched kale or cut pieces thereof of this invention may be 80 mg/100 g or more, or 100 mg/100 g or more. It may further be 200 mg/100 g or more, or even 250 mg/100 g or more.

Second invention: Cruciferous plant, cut pieces thereof, or juice of the plant or cut pieces containing GABA in an amount of 10 mg/100 g or more and maintaining green color by blanching.

The cruciferous plant of the second invention is obtained by blanching a GABA-enriched cruciferous plant.

The cut pieces of the cruciferous plant of the second invention are obtained by first blanching a GABA-enriched cruciferous plant and then cutting the blanched GABA-enriched cruciferous plant into pieces, or by first cutting a cruciferous plant into pieces, then subjecting the cut pieces to GABA enrichment, and blanching the GABA-enriched cut pieces.

The juice of the cruciferous plant of the second invention is obtained by squeezing a GABA-enriched, then blanched cruciferous plant or cut pieces thereof, or by blanching juice obtained by squeezing a GABA-enriched cruciferous plant or cut pieces thereof.

By the blanching with extremely hot water, GABA in the cruciferous plant is mostly lost. In case of non-GABA enriched cruciferous plant, the GABA content of the cruciferous plant is reduced to 5 mg/100 g or less). However, by performing GABA enrichment before the blanching, 10 mg/100 g or more of GABA remains in the cruciferous plant.

Third invention: Dried powder of cruciferous plant or cut pieces thereof containing GABA in an amount of 180 mg/100 g or more.

Dried powder of a cruciferous plant or cut pieces thereof of the third invention is obtained by drying a GABA-enriched cruciferous plant or cut pieces thereof.

In general, among the cruciferous plants, kale has a highest GABA content, which is about 30 mg/100 g, that is, the GABA content of the dried powder of kale is about 170 mg/100 g. However, there has never existed such cruciferous plant dried powder having a GABA content of 180 mg/100 g or more as that of this invention, which is therefore novel.

Dried powder having a required GABA content can be obtained by appropriately selecting the specific method and conditions for the GABA enrichment. For example, dried powder having a GABA content of 300 mg/100 g or more, 400 mg/100 g or more, 500 mg/100 g or more, 1000 mg/100 g or more, or 1500 mg/100 g or more may be obtained. Even dried powder having a GABA content of about 4000 mg/100 g may be obtained.

Fourth invention: Dried powder of cruciferous plant or cut pieces thereof containing GABA in an amount of 10 mg/100 g or more and maintaining green color.

Dried powder of a cruciferous plant or cut pieces thereof of the fourth invention is obtained by subjecting a cruciferous plant or cut pieces thereof to microwave radiation. By performing the microwave radiation after GABA enrichment, the resultant cruciferous plant contains GABA in a higher concentration.

As will be apparent from the examples described later, the GABA content in a non-GABA-enriched cruciferous plant or cut pieces thereof decreases by blanching to as small as about 2 mg/100 g. By adopting the microwave radiation treatment in place of blanching, however, the resultant cruciferous plant has a GABA content of 10 mg/100 g or more, or even 20 mg/100 g or more, while maintaining the green color. Moreover, by combining the microwave radiation with the GABA enrichment, obtained is a cruciferous plant having a GABA content of 50 mg/100 g or more and maintaining the green color.

Green cruciferous plants intrinsically contain GABA in an amount of about 30 mg/100 g as described above. Therefore, the cruciferous plant that has a GABA content of 50 mg/100 g or more and still has the green color of this invention is novel.

A cruciferous plant having a required GABA content can be obtained by appropriately selecting the specific method and conditions for the GABA enrichment. For example, a cruciferous plant having a GABA content of 70 mg/100 g or more, 100 mg/100 g or more, 150 mg/100 g or more, or 200 mg/100 g or more may be obtained. Even a cruciferous plant having a GABA content of about 500 mg/100 g may be obtained as an upper limit.

Since the GABA enrichment and the microwave radiation are comparatively moderate treatments, vitamins, especially vitamin B1 and vitamin C, contained in a cruciferous plant are retained without being lost after drying. Specifically, preferably, vitamin B1 and vitamin C may be contained in amounts of 0.1 mg/100 g or more and 100 mg/100 g or more, respectively, in the cruciferous plant maintaining the green color.

The cruciferous plant containing GABA in an amount of 510 mg/100 g or more and maintaining green color can also be obtained by first subjecting a cruciferous plant to GABA enrichment and then blanching the GABA-enriched plant.

Fifth invention: Dried powder of juice of cruciferous plant containing GABA in an amount of 350 mg/100 g or more.

Dried powder of juice of the fifth invention is obtained by drying juice of a GABA-enriched cruciferous plant or cut pieces thereof, or by drying juice of a cruciferous plant after the juice is subjected to GABA enrichment.

In general, among the cruciferous plants, kale has a highest GABA content, which is about 30 mg/100 g. When juice of kale is dried and pulverized, the GABA content of the dried powder is about 340 mg/100 g. Therefore, there has never existed such juice dried powder having a GABA content of 350 mg/100 g or more that is obtained by drying juice of a GABA-enriched cruciferous plant or GABA-enriched juice as that of this invention, which is therefore novel.

By appropriately selecting the specific method and conditions for the GABA enrichment, a cruciferous plant, especially kale, may have a GABA content in the range of 350 to 4000 mg/100 g. The GABA content may be preferably 500 mg/100 g or more, more preferably 800 mg/100 g or more, still more preferably 1000 mg/100 g or more, most preferably 1500 mg/100 g. In a preferred case, dried powder of juice of kale may contain GABA six times as much as that contained in the conventional juice dried powder.

Sixth invention: Juice of cruciferous plant containing GABA in an amount of 50 mg/100 g or more and maintaining a green color.

Juice of a cruciferous plant containing GABA in an amount of 150 mg/100 g or more and maintaining a green color of the sixth invention is obtained by subjecting a cruciferous plant to GABA enrichment and microwave radiation in combination and squeezing the treated cruciferous plant. The microwave radiation may be performed before or after the GABA enrichment.

The juice of the sixth invention may also be obtained by first squeezing a cruciferous plant to obtain juice and subjecting the juice to GABA enrichment and microwave radiation in combination.

The cruciferous plants intrinsically contain GABA only in an amount of about 30 mg/100 g as described above. Therefore, the juice of a cruciferous plant containing GABA in an amount of 50 mg/100 g or more and maintaining a green color of this invention is novel.

Juice of a cruciferous plant having a required GABA content can be obtained by appropriately selecting the specific method and conditions for GABA enrichment. For example, juice of a cruciferous plant having a GABA content of 70 mg/100 g or more, 100 mg/100 g or more, 200 mg/100 g or more, or 300 mg/100 g or more may be obtained. Even juice of a cruciferous plant having a GABA content of about 600 mg/100 g may be obtained as an upper limit.

As described above, the juice of a cruciferous plant maintaining green color of this invention preferably contains vitamin B1 and vitamin C in amounts of 0.1 mg/100 g or more and 100 mg/100 g or more, respectively.

Seventh invention: Dried powder of cruciferous plant or cut pieces thereof containing GABA in an amount of 10 mg/100 g or more and maintaining a green color.

Dried powder of the seventh invention is obtained by subjecting a cruciferous plant to microwave radiation. As will be apparent from the examples described later, green dried powder obtained by blanching (with extremely hot water) a non-GABA enriched cruciferous plant contains GABA only in an amount of about 2 mg/100 g. By adopting microwave radiation, the resultant green dried powder of a cruciferous plant contains GABA in an amount of 10 mg/100 g or more. Therefore, the dried powder of a cruciferous plant that has a GABA content of 10 mg/100 g or more and maintains a green color is novel.

When the cruciferous plant is kale, the GABA content may be 20 mg/100 g or more, 100 mg/100 g or more, or even 150 mg/100 g or more. By combining the microwave radiation with GABA enrichment, the GABA content may be as high as 200 mg/100 g or more, or even 500 mg/100 g or more.

As in the above inventions, dried powder of a cruciferous plant maintaining a green color of this invention preferably contains vitamin B1 and vitamin C in amounts of 0.1 mg/100 g or more and 100 mg/100 g or more, respectively.

The dried powder of the seventh invention may also be obtained by first subjecting a cruciferous plant to GABA enrichment land then blanching the GABA-enriched plant.

Eighth invention: Dried powder of juice of cruciferous plant containing GABA in an amount of 10 mg/100 g or more and maintaining a green color.

Dried powder of juice of the eighth invention is obtained by subjecting a cruciferous plant or juice thereof to microwave radiation. As described above, green dried powder obtained by blanching (with extremely hot water) a non-GABA-enriched cruciferous plant contains GABA only in an amount of about 2 mg/100 g. Juice of the cruciferous plant therefore will not have a concentration of GABA exceeding about 2 mg/100 g. Therefore, the dried powder of juice of a cruciferous plant that has a GABA content of 10 mg/100 g or more and maintains a green color is novel.

When the cruciferous plant is kale, the GABA content of dried powder of juice of kale may be 20 mg/100 g or more, 100 mg/100 g or more, or even 150 mg/100 g or more. By combining the microwave treatment with GABA enrichment, the GABA content may be as high as 200 mg/100 g or more, or even 500 mg/100 g or more.

As in the above inventions, dried powder of juice of a cruciferous plant maintaining a green color of this invention preferably contains vitamin B1 and vitamin C in amounts of 0.1 mg/100 g or more land 100 mg/100 g or more, respectively.

The dried powder of juice of a cruciferous plant containing GABA in an amount of 10 mg/100 g or more and maintaining a green color of this invention may also be obtained by first subjecting juice of the cruciferous plant to GABA enrichment, then blanching the GABA enriched juice, and drying the juice.

Sterilization

The cruciferous plants, juice thereof, and dried powder of the plants and the juice obtained in the various manners described above are sterilized as required by a method using airflow, high pressure, heating, or the like.

Usage

The cruciferous plants, cut pieces thereof, juice of the plants and the cut pieces, and dried powder of the plants, the cut pieces, and the juice obtained in the manners described above, which have various GABA contents, can be used as they are, as foods, beverages, and materials thereof, as medicine materials, and as feed for animals such as livestock and pets.

Moreover, the cruciferous plants, cut pieces thereof, juice of the plants and the cut pieces, and dried powder of the plants, the cut pieces, and the juice, which have various GABA contents, may be mixed with an excipient, an expander, a binder, a thickener, an emulsifier, a colorant, a perfume, a food additive, a seasoning, and the like as required, and may be formed into shapes of powder, granules, capsules such as hard capsules and soft capsules, tablets, pills, tea-leaves, tea bags, candy bars, and the like.

For example, royal jelly, vitamin, protein, calcium, chitosan, lecithin, and the like may be blended, and honeydew and a seasoning may be added to correct the taste. The resultant products may be formed into various shapes as described above as required, to be used as foods. These foods may be ingested directly or may be dissolved in water, hot water, milk, or the like for drinking. Otherwise, their ingredients may be leached out for drinking.

The GABA-enriched cruciferous plants, juice thereof, and dried powder of the plants and the juice obtained by the method according to the present invention may be used as a material for isolating and purifying GABA. In particular, kale is useful as the material for this purpose.

EXAMPLES

Hereinafter, the present invention will be described by way of example. Note that the following examples are not intended to restrict the scope of the present invention. The GABA amount was measured with an automatic amino acid analyzer under the following conditions.

Machine type: JLC-500/V (JEOL Ltd.)

Column: LCR-6, 4 mm×90 mm (JEOL Ltd.)

Mobile phase: Lithium citrate buffer (JEOL Ltd.)
P-21 (pH 2.98, Li 0.105 mol/l) 0→16.3 min
P-12 (pH 3.28, Li 0.26 mol/l) 16.3→36.1 min
P-13 (pH 3.46, Li 0.80 mol/l) 36.1→56.0 min
P-14 (pH 2.83, Li 1.54 mol/l) 56.0→63.4 min
P-15 (pH 3.65, Li 1.54 mol/l) 63.4→80.0 min Reaction solution: Ninhydrin-hydrindantin reagent (Wako Pure Chemical Industries, Ltd.)

Temperature: Column 35° C.(0→16.3 min), 64° C.(15.3→31.0 min) 44° C.(31.0→44.4 min), 72° C.(63.4→80.0 min)

Reaction bath 135° C.

Flow rate: Mobile phase 0.50 ml/min
Reaction solution 0.30 ml/min

Measured wavelength: 570 nm

Example 1

Raw leaves of kale and cabbage and about 5 mm pieces of broccoli were subjected to infrared treatment. Specifically, the object to be treated was sealed to prevent moisture thereof from evaporating and exposed to infrared radiation for one hour using a 400 W infrared radiation apparatus while controlling the inner temperature of the object to be kept at 40° C. using a temperature sensor inserted in the object. After the infrared treatment, the GABA content was measured with an automatic amino acid analyzer. The measurement results are shown in Table 1 below.

TABLE 1

| Material | Before treatment GABA content (mg/100 g) | After treatment GABA content (mg/100 g) | GABA increase rate (%) |
| --- | --- | --- | --- |
| Kale leaves | 30 | 186 | 620 |
| Cabbage leaves | 15 | 88 | 587 |
| Broccoli | 8 | 29 | 363 |

As is found from Table 1, the GABA contents in the cruciferous plants increased by the thermal retention treatment. The GABA content increased about 3.6 times for broccoli, about 5.9 times for cabbage, and about 6.2 times for kale.

Example 2

Raw leaves of kale were treated with infrared, warm air, and hot water individually. The infrared treatment followed the procedure described in Example 1. In the warm air treatment, the object was exposed to 40° C. warm air in an incubator under the sealed conditions. In the hot water treatment, the object was put in 40° C. hot water. After the respective treatments, the GABA content was measured. The measurement results are shown in Table 2 below.

TABLE 2

| Means for thermal Retention | GABA content (mg/100 g · wet weight) | GABA increase rate (%) |
|---|---|---|
| (before treatment) | 29 | (100) |
| Infrared | 193 | 666 |
| Warm air | 93 | 321 |
| Hot water | 110 | 379 |

As is found from Table 2, the GABA content in the kale leaves increased by the thermal retention treatment irrespective of the means used for the thermal retention. In particular, using infrared, the GABA content increased about 6.7 times. Using warm air and hot water, the GABA content increased about 3.2 times and 3.8 times, respectively.

Example 3

Raw leaves of kale, 5 mm pieces of the kale leaves, and juice of kale obtained by crushing the kale leaves with a mixer and filtering the crushed leaves. were subjected to the infrared treatment described in Example 1 at 40° C. for one hour. After the treatment, the GABA content was measured. The results are shown in Table 3 below.

TABLE 3

| | Before infrared treatment GABA content (mg/100 g) | After infrared treatment GABA content (mg/100 g) | GABA increase rate (%) |
|---|---|---|---|
| Raw leaves | 29 | 180 | 621 |
| Cut pieces | 27 | 186 | 689 |
| Juice | 38 | 281 | 739 |

As is found from Table 3, the GABA contents increased in all the objects, i.e., the raw leaves, the cut leaf pieces, and the juice, by the GABA-enriching treatment six to seven times or more than the GABA contents before the treatment.

Example 4

Since the infrared treatment was found effective, the optimum temperature for the infrared treatment was examined. Kale raw leaves were subjected to infrared radiation at various temperatures shown in Table 4 below and the resultant GABA contents were measured. The results are shown in Table 4.

TABLE 4

| Temperature (° C.) | GABA content (mg/100 g · wet weight) | GABA increase rate (%) |
|---|---|---|
| (Before treatment) | 31 | (100) |
| 25 | 33 | 106 |
| 30 | 87 | 281 |
| 35 | 139 | 448 |
| 40 | 208 | 671 |
| 45 | 78 | 252 |
| 50 | 39 | 126 |
| 55 | 28 | 90 |

As is found from Table 4, the optimum temperature is around 40° C. the GABA content tends to decrease when the temperature is 25° C. or lower or 55° C. or higher.

Example 5

Since the infrared treatment at 40° C. was found effective, the optimum duration of the infrared treatment was examined. Kale raw leaves were subjected to infrared radiation at 40° C. for various durations shown in Table 5 below and the resultant GABA contents were measured. The results are shown in Table 5.

TABLE 5

| Duration | GABA content (mg/100 g · wet weight) | GABA increase rate (%) |
|---|---|---|
| (Before treatment) | 38 | (100) |
| 10 minutes | 43 | 113 |
| 30 minutes | 105 | 276 |
| 60 minutes | 247 | 650 |
| 6 hours | 257 | 676 |
| 12 hours | 245 | 645 |
| 24 hours | 234 | 616 |

As is found from Table 5, the GABA content tends to increase ten minutes after the start of the treatment. The GABA content increased about three times after 30 minutes and reached the highest value after about one to six hours.

Example 6

The effect of the anaerobic treatment on the increase in GABA content was examined using kale raw leaves. As the anaerobic treatment, kale raw leaves were packed in a vinyl bag, which was deflated and then filled with nitrogen gas. The resultant bag was placed in an incubator and kept at 25° C. for various durations shown in Table 6 below. As for the treatment at 40° C. shown in Table 6, infrared radiation was performed under the anaerobic conditions. The results are shown in Table 6.

TABLE 6

| Temperature (° C.) | Duration (hour) | GABA content (mg/100 g · wet weight) | GABA increase rate (%) |
|---|---|---|---|
| (Before treatment) | | 24 | (100) |
| 25 | 6 | 71 | 296 |
| | 12 | 92 | 383 |
| | 24 | 83 | 346 |
| 40 | 24 | 177 | 738 |

As is found from Table 6, the anaerobic treatment at 25° C. increased the GABA content in the kale raw leaves three times or more, proving that the GABA content also increases by the anaerobic treatment. It is also found that the GABA content increased about 7.4 times by the 40° C. thermal retention treatment (infrared treatment).

Example 7

Kale raw leaves were subjected to 40° C. one-hour thermal retention treatment (infrared treatment), and then dried with a dryer at 60° C. so that the moisture content was reduced to 5% or less. The resultant leaves were crushed with a blender to obtain GABA-enriched kale dried powder. Kale raw leaves that had not been subjected to the thermal retention treatment were also processed in the above manner to obtain non-GABA-enriched kale dried powder. The GABA contents in the respective dried powders were measured. The results are shown in Table 7 below.

TABLE 7

| GABA enrichment | GABA content (mg/100 g) | GABA increase rate (%) |
| --- | --- | --- |
| Enriched | 1482 | 867 |
| Non-enriched | 171 | (100) |

As is found from Table 7, the GABA content in the GABA-enriched dried powder increased about 8.7 times.

Example 8

Kale raw leaves were subjected to 40° C. one-hour thermal retention treatment (infrared treatment) and then crushed with a mixer to produce juice. The resultant juice was filtrated to remove fibrous substances, to obtain GABA-enriched kale juice. Kale raw leaves that had not been subjected to the thermal retention treatment were also processed in the above manner to obtain non-GABA-enriched kale juice. The GABA contents in the respective juices were measured. The results are shown in Table 8 below.

TABLE 8

| GABA enrichment | GABA content (mg/100 g) | GABA increase rate (%) |
| --- | --- | --- |
| Enriched | 273 | 650 |
| Non-enriched | 42 | (100) |

As is found from Table 8, by the GABA enrichment the GABA content in the juice increased 6.5 times.

Example 9

Kale raw leaves were subjected to 40° C. one-hour thermal retention treatment (infrared treatment) and then crushed with a mixer to produce juice. The resultant juice was filtrated to remove fibrous substances, to obtain GABA-enriched kale juice. The GABA-enriched kale juice was freeze-dried and then crushed with a blender, thereby to obtain GABA-enriched kale juice dried powder. Kale raw leaves that had not been subjected to the thermal retention treatment were also processed in the above manner to obtain non-GABA-enriched kale juice dried powder. The GABA contents in the respective juice dried powders were measured. The results are shown in Table 9 below.

TABLE 9

| GABA enrichment | GABA content (mg/100 g) | GABA increase rate (%) |
| --- | --- | --- |
| Enriched | 1638 | 964 |
| Non-enriched | 170 | (100) |

As is found from Table 9, the GABA content in the GABA-enriched juice dried powder increased about 9.6 times.

Example 10

Young leaves of kale were picked, washed with water, drained, and cut into about 3 cm square pieces. A hundred grams of the cut leaf pieces were subjected to microwave treatment with a 2450 MHz, 500 W power apparatus (microwave oven RE-121 of Sharp Corp.) for various durations shown in Table 10 below. The resultant leaf pieces were dried at 60° C. for six hours with a dryer (MOV-112S of Sanyo Electric Co., Ltd.) and crushed with a blender to obtain kale powder having a moisture content of 5% or less.

Comparative Example 1

A hundred grams of cut kale leaf pieces were put in 1 L of 95° C. hot water and left for three minutes. The leaf pieces were then swiftly moved to 5° C. cold water and immersed therein for about five minutes. After cooling, the leaf pieces were dehydrated with a centrifuge for about 45 seconds, followed by the drying and powdering in the manner described in Example 10. The drying took ten hours in this case.

Comparative Example 2

A hundred grams of cut kale leaf pieces were put in 1 L of 95° C. hot water containing 7.5 g of salt and 7.5 g of sodium bicarbonate. The resultant leaf pieces were dried and powdered as in Comparative Example 1.

The results are shown in Table 10. In Table 10, the "non-treated" refers to the process that cut kale leaves were crushed with a blender to obtain powder directly and after being dried at 60° C. for six hours. The unit of values in Table 10 is mg/100 g in terms of dry weight. The vitamins were measured by high-performance liquid chromatography.

TABLE 10

| | Non-treated | Microwave treatment | | | | | Blanching | |
| --- | --- | --- | --- | --- | --- | --- | --- | --- |
| | | 1 0.5 min | 2 1 min | 3 3 min | 4 5 min | 5 10 min | 1 3 min | 2 3 min |
| GABA | 171* | 170 | 169 | 152 | 145 | 23 | 4.3 | 5.1 |
| Vitamin B1 | 0.49 | 0.48 | 0.47 | 0.42 | 0.41 | 0.38 | 0.04 | 0.03 |
| Vitamin C | 188 | 188 | 185 | 170 | 152 | 121 | 12 | 10 |

*Values in terms of dry weight

As is found from Table 10, the microwave-treated cruciferous plant (kale) well sustained GABA, as well as vitamin B1 and vitamin C, compared with the plants subjected to the conventional blanching with extremely hot water or sodium bicarbonate-added salt water.

The microwave-treated kale and conventionally-treated kale packed in aluminum packages for light shading were left in an environment of a temperature of 40° C. and a humidity of 75% for two months. As a result, the microwave-treated kale preserved the vivid green color from fading, but the non-treated kale was faded from the green color to a slightly brownish color.

Example 11

Kale raw leaves were picked and subjected to 40° C. one-hour infrared treatment. Specifically, the leaves were sealed to prevent moisture thereof from evaporating and exposed to infrared radiation using an infrared radiation apparatus while controlling the inner temperature to be kept at 40° C. The resultant leaves were blanched with extremely hot water and then dried in the manner described in Example 7 to obtain dried powder. Also, 3 cm square pieces of the kale raw leaves were subjected to infrared treatment as described above for GABA enrichment. The resultant leaf pieces were blanched with extremely hot water and then squeezed to obtain juice. The juice was dried to obtain powder. The GABA contents of the thus GABA-enriched and blanched kale leaves, juice, dried powder of the kale leaves, and dried powder of the juice were measured.

For comparison, kale leaves were blanched with extremely hot water without GABA enrichment, then dried, and pulverized, to obtain dried powder. The results are shown in Table 11 below.

TABLE 11

| Kale | Treatment | GABA content (mg/100 g) | |
|---|---|---|---|
| 1 Leaves | Blanching | 1.5 | Wet weight |
| 2 Leaves | GABA enriching-Blanching | 10.1 | Wet weight |
| 3 Juice | GABA enriching-Blanching | 14.1 | Wet weight |
| 4 Dried powder of leaves | Blanching - Drying | 5.2 | Dry weight |
| 5 Dried powder of leaves | GABA enriching-blanching-drying | 67.0 | Dry weight |
| 6 dried powder of juice | GABA enriching-blanching-drying | 85.0 | Dry weight |

As is found from Table 11, by performing the treatments of GABA enrichment and blanching in combination, GABA, which was conventionally lost mostly by blanching, remained in a much greater amount. Even in the form of leaves, GABA remained in an amount of 10 mg/100 g or more. More specifically, in the comparative example where no GABA enriching treatment was performed, only 1.5 mg/100 g of GABA remained in the kale leaves and 5.2 mg/100 g in the dried powder. On the contrary, in the example of the present invention, 10.1 mg/100 g of GABA remained in the kale leaves, 14.1 mg/100 g in the juice, 67 g/100 g in the dried powder of the kale leaves, and 85 mg/100 g in the dried powder of the juice.

Example 12

Kale raw leaves were picked and subjected to the infrared treatment described in Example 11 for GABA enrichment. Thereafter, microwave radiation and drying were performed in the manner described in Example 10. For comparison, kale leaves were blanched with extremely hot water without GABA enrichment, then dried, and pulverized, to obtain dried powder. The GABA contents of the resultant powders were measured, and the results are shown in Table 12 below. Note that the leaves shown in Table 12 were obtained by the microwave treatment only, while the dried powder was obtained by the microwave treatment and the subsequent drying. The values are therefore in terms of wet weight for the leaves and dry weight for the dried powder.

TABLE 12

| | Microwave treatment duration (minute) | GABA content (mg/100 g) |
|---|---|---|
| Leaves | — | 1.4* |
| | 0.5 | 210 |
| | 1 | 201 |
| | 3 | 185 |
| | 5 | 174 |
| Dried Powder | — | 5.2* |
| | 0.5 | 1267 |
| | 1 | 1211 |
| | 3 | 1118 |
| | 5 | 1054 |

*Blanching without GABA enrichment

As is found from Table 12, by the method according to the present invention, GABA was obtained in a concentration as high as 1200 mg/100 g. That is, the present invention provides dried powder of a cruciferous plant that contains GABA in an amount 240 times as much as that conventionally obtained and maintains a green color.

From the above examples, the following is found. In the conventional method, GABA, vitamin B1, and vitamin C of kale are mostly lost although the green color of the kale is kept from fading. On the contrary, GABA, vitamin B1, and vitamin C mostly remain in the kale subjected to the microwave treatment. This proves the usefulness of the cruciferous plant according to the present invention.

Example 13

Kale was washed with water to remove attachments such as dirt, and cut into about 5 cm square pieces. The kale pieces, 200 g, were immersed in a 3% sodium glutamate solution (2 L), incubated for four hours at various temperatures shown in Table 13 below, and then washed with water. The resultant leaf pieces were freeze-dried and then crushed to such a degree that about 90% of the leaf pieces could pass through a 200-mesh sieve to obtain powdery dried products. The GABA contents of the resultant powdery dried products were measured, and the test results are shown in Table 13.

The "non-treated" in Table 13 refers to kale raw leaves that were directly processed into a powdery dried product without being immersed in a sodium glutamate solution nor being blanched. The "GABA enriched rate" refers to the rate of the GABA content in each sample with respect to the GABA content in the non-treated kale as 1.

TABLE 13

| Temperature (° C.) | GABA content (mg/100 g) | GABA enriched rate |
|---|---|---|
| Non-treated | 170 | (1) |
| 10 | 187 | 1.1 |
| 20 | 663 | 3.9 |
| 25 | 1071 | 6.3 |
| 30 | 1122 | 6.6 |
| 40 | 1105 | 6.5 |
| 50 | 629 | 3.7 |
| 60 | 204 | 1.2 |

As is found from Table 13, by immersing in the 3% sodium glutamate solution, GABA was enriched at temperatures in a wide range. In particular, the GABA content increased most significantly at temperatures of 30 to 40° C.

Example 14

Kale cut into about 5 cm square pieces, 200 g, was used as the material as in Example 13. The kale pieces were immersed in 3% sodium glutamate solutions (each 2 L) adjusted to various pH values shown in Table 14 below, and then washed with water. The resultant leaf pieces were freeze-dried, and then crushed to such a degree that about 90% of the leaf pieces could pass through a 200-mesh sieve, to obtain powdery dried products. The GABA contents of the powdery dried products were measured, and the results are shown in Table 14. For comparison, kale raw leaves were directly processed into a powdery dried product without being immersed in a sodium glutamate solution nor being blanched with extremely hot water. Such a powdery dried product is shown in Table 14 as "non-treated".

TABLE 14

| pH | GABA content (mg/100 g) | GABA enriched rate |
|---|---|---|
| Non-treated | 170 | (1) |
| 4.0 | 1020 | 6.0 |
| 5.0 | 1377 | 8.1 |
| 6.0 | 1547 | 9.1 |
| 7.0 | 986 | 5.8 |
| 8.0 | 340 | 2.0 |
| 9.0 | 187 | 1.1 |

As is found from Table 14, although no limit is specifically set for the pH of the immersion solution, a value of about 4.0 to about 6.0 is preferable.

Example 15

Kale was cut into about 5 cm square pieces as in Example 13, and 200 g of the resultant kale pieces were immersed in sodium glutamate solutions adjusted to various concentrations shown in Table 15 below at 30° C. for four hours, and then washed with water. The resultant leaf pieces were freeze-dried, and then crushed to such a degree that about 90% of the leaf pieces could pass through a 200-mesh sieve, to obtain powdery dried products. The GABA contents of the powdery dried products were measured, and the results are shown in Table 15. For comparison, kale raw leaves were directly processed into a powdery dried product without being immersed in a sodium glutamate solution nor being blanched with extremely hot water. Such a powdery dried product is shown in Table 15 as "non-treated".

TABLE 15

| Concentration (%) | GABA content (mg/100 g) | GABA enriched rate |
|---|---|---|
| Non-treated | 170 | (1) |
| 0.01 | 340 | 2.0 |
| 0.05 | 527 | 3.1 |
| 0.1 | 748 | 4.4 |
| 0.2 | 935 | 5.5 |
| 0.5 | 1088 | 6.4 |
| 1 | 1156 | 6.8 |
| 3 | 1207 | 7.1 |
| 10 | 1258 | 7.4 |
| 20 | 1326 | 7.8 |

As is found from Table 15, GABA in the kale increases by immersing the kale in a sodium glutamate solution, and the GABA content varies with the concentration of the solution.

Example 16

Kale was cut into about 5 cm square pieces as in Example 13, and 200 g of the kale pieces were immersed in a 10% sodium glutamate solution adjusted to pH 6.0 at 30° C. for various durations shown in Table 16 below and then washed with water. The resultant leaf pieces were freeze-dried and then crushed to such a degree that about 90% of the leaf pieces could pass through a 200-mesh sieve, to obtain powdery dried products. The GABA contents of the powdery dried products were measured, and the results are shown in Table 16. For comparison, kale raw leaves were directly processed into a powdery dried product without being immersed in a sodium glutamate solution nor being blanched with extremely hot water. Such a powdery dried product is shown in Table 16 as "non-treated".

TABLE 16

| Duration (hour) | GABA content (mg/100 g) | GABA enriched rate |
|---|---|---|
| Non-treated | 170 | (1) |
| 0.5 | 850 | 5.0 |
| 1 | 1108 | 6.5 |
| 5 | 1394 | 8.2 |
| 10 | 1309 | 7.7 |

As is found from Table 16, GABA is sufficiently enriched by incubation of 30 minutes or more.

Example 17

Commercially available dried sea tangle, 50 g, was immersed in 1.5 L water, and warmed to prepare stock. The stock was filtered with a gauze, and cooled. In the resultant stock (1 L) that was adjusted to pH 6.0, 100 g of kale cut into about 5 cm square pieces as in Example 13 was immersed for four hours at 40° C., and then washed with water. The kale pieces were freeze-dried, and then crushed to such a degree that about 90% of the leaf pieces could pass through a 200-mesh sieve, to obtain a powdery dried product. The GABA content of the powdery dried product was measured, and the results are shown in Table 17 below. For comparison, kale raw leaves were directly processed into a powdery dried product without being immersed in a sodium glutamate solution nor being blanched with extremely hot water. Such a powdery dried product is shown in Table 17 as "non-treated".

TABLE 17

| Food material | GABA content (mg/100 g) | GABA enriched rate |
|---|---|---|
| Non-treated | 170 | (1) |
| Dried sea tangle | 204 | 1.2 |

As is found from Table 17, GABA is also enriched by using a glutamic acid-containing food material.

Example 18

Leaves of kale, cabbage, and broccoli were cut into about 5 cm square pieces. The leaf pieces were immersed in a 10% sodium glutamate solution adjusted to pH 6.0 for four hours at 30° C., and then washed with water. The resultant leaf pieces were freeze-dried and then crushed to such a degree that about 90% of the leaf pieces could pass through a 200-mesh sieve, to obtain powdery dried products. The GABA contents of the powdery dried products were measured, and the results are shown in Table 18 below. For comparison, kale, cabbage, and broccoli raw leaves were directly processed into powdery dried products without being immersed in a sodium glutamate solution nor being blanched with extremely hot water. Such powdery dried products are shown in Table 18 as "non-treated".

TABLE 18

| Plant | GABA content (mg/100 g) Non-treated | GABA content (mg/100 g) After enrichment | GABA enriched rate |
|---|---|---|---|
| Kale | 170 | 1122 | 6.6 |
| Cabbage | 78 | 460 | 5.9 |
| Broccoli | 26 | 211 | 8.1 |

As is found from Table 18, the GABA enrichment according to the present invention is effective for not only kale but also other cruciferous plants, i.e., cabbage and broccoli.

Example 19

Kale was washed with water to remove attachments such as dirt, and cut into about 5 cm square pieces. The kale pieces, 200 g, were immersed in a 3% sodium glutamate solution (2 L), incubated for four hours at 30° C., and washed with water. The resultant leaf pieces were subjected to microwave radiation with a 2450 MHz, 500 W power apparatus for one minute, and then crushed with a juicer to obtain slurry. The slurry was freeze-dried, to obtain a powdery dried product.

Example 20

Kale was GABA-enriched using a sodium glutamate solution in the manner described in Example 19. The resultant kale pieces were washed with water, squeezed, and filtered to obtain juice. The juice was subjected to microwave radiation with a 2450 MHz, 500 W power apparatus for one minute, and then freeze-dried, to obtain a powdery dried product.

The GABA contents in the powdery dried products obtained in Examples 19 and 20 were measured, and the results are shown in Table 19 below. The "non-treated" in Table 19 refers to kale leaves that were blanched with extremely hot water without being immersed in a sodium glutamate solution, to obtain a powdery dried product. The "GABA enriched rate" refers to the rate of the GABA content in each example with respect to the GABA content in the non-treated kale as 1.

TABLE 19

|  | GABA content (mg/100 g) | GABA enriched rate |
|---|---|---|
| Non-treated | 5 | (1) |
| Example 19 | 1055 | 211 |
| Example 20 | 1100 | 220 |

As is found from Table 19, the GABA content was retained after the microwave treatment. Furthermore, the resultant dried products maintained vivid green color. The non-treated products also maintained vivid green color after pulverizing by the blanching with extremely hot water. However, during the blanching, a large amount of GABA eluted in the hot water, resulting in reducing the GABA content.

Example 21

Kale was washed with water to remove attachments such as dirt, and cut into about 5 cm square pieces. The kale pieces were further crushed into cut pieces having a mean diameter of about 0.5 mm with a wet process crusher. By this crushing, almost all cut pieces had a mean diameter of 1 mm or less. Thereafter, the cut pieces were squeezed and filtered to remove fibrous components, to obtain juice. To the juice (100 ml), a 30% sodium glutamate solution was added so that the final concentration of the sodium glutamate was 3%. The resultant solution was stirred for four hours at various temperatures shown in Table 20 below, then freeze-dried, and crushed to such a degree that about 90% of crushed pieces could pass through a 200-mesh sieve, to obtain powdery dried products. The GABA contents of the powdery dried products were measured with an automatic amino acid analyzer. The results are shown in Table 20. The "non-treated" in Table 20 refers to the juice of kale raw leaves obtained by squeezing the kale cut pieces which was directly freeze-dried without the addition of a sodium glutamate solution to the juice, then dried and powdered. The "GABA enriched rate" refers to the rate of the GABA content in each example with respect to the GABA content in the non-treated kale as 1.

TABLE 20

| Temperature (° C.) | GABA content (mg/100 g) | GABA enriched rate |
|---|---|---|
| Non-treated | 340 | (1) |
| 10 | 374 | 1.1 |
| 20 | 1530 | 4.5 |
| 25 | 2312 | 6.8 |
| 30 | 2482 | 7.3 |
| 40 | 2346 | 6.9 |
| 50 | 1462 | 4.3 |
| 60 | 408 | 1.2 |

As is found from Table 20, GABA is enriched with the immersion solution at temperatures in a wide range. In particular, for the 3% sodium glutamate solution, the GABA content increased most significantly when the temperature of the solution was about 30° C.

Example 22

To the kale juice (100 ml) obtained in the manner described in Example 21, a 30 wt. % sodium glutamate solution was added so that the final concentration of the sodium glutamate was 3%, and the resultant solution was adjusted with citric acid or sodium carbonate to have various pH values shown in Table 21 below. The resultant solutions were stirred for four hours while keeping at 30° C., then freeze-dried, and crushed to such a degree that about 90% of crushed pieces could pass through a 200-mesh sieve, to obtain powdery dried products. The GABA contents of the powdery dried products were measured, and the results are shown in Table 21. For comparison, the kale juice was processed into a powdery dried product without adding a sodium glutamate solution to the juice. Such a powdery dried product is shown in Table 21 as "non-treated".

TABLE 21

| pH | GABA content (mg/100 g) | GABA enriched rate |
|---|---|---|
| Non-treated | 340 | (1) |
| 4.0 | 2278 | 6.7 |
| 5.0 | 3366 | 9.9 |
| 6.0 | 2992 | 8.8 |
| 7.0 | 2108 | 6.2 |
| 8.0 | 714 | 2.1 |
| 9.0 | 374 | 1.1 |

As is found from Table 21, although no limit is specifically set for the pH of the immersion solution, pH of about 5.0 is preferable.

Example 23

To the kale juice obtained in the manner described in Example 21, a sodium glutamate solution was added so as to obtain various final concentrations of sodium glutamate shown in Table 22 below. The resultant solutions were adjusted to pH 5.0 with citric acid. The solutions were stirred for four hours while keeping at 30° C., then freeze-dried, and crushed to such a degree that about 90% of crushed pieces could pass through a 200-mesh sieve, to obtain powdery dried products. The GABA contents of the powdery dried products were measured, and the results are shown in Table 22. For comparison, the kale juice was processed into a powdery dried product without adding a sodium glutamate solution to the juice. Such a powdery dried product is shown in Table 22 as "non-treated".

TABLE 22

| Concentration (%) | GABA content (mg/100 g) | GABA enriched rate |
|---|---|---|
| Non-treated | 340 | (1) |
| 0.01 | 714 | 2.1 |
| 0.05 | 1088 | 3.2 |
| 0.1 | 1462 | 4.3 |
| 0.2 | 1870 | 5.5 |
| 0.5 | 2040 | 6.0 |
| 1 | 2108 | 6.2 |
| 3 | 2176 | 6.4 |
| 10 | 2414 | 7.1 |
| 20 | 2652 | 7.8 |

As is found from Table 22, GABA increases by adding a sodium glutamate solution to the kale juice and the GABA content varies with the concentration of the solution.

Example 24

To the kale juice obtained in the manner described in Example 21, a 30 wt. % sodium glutamate solution was added so that the final concentration of sodium glutamate was 3%. The resultant solution was adjusted to pH 5.0 with citric acid. The solution was stirred for various durations shown in Table 23 below while keeping at 30° C., then freeze-dried, and crushed to such a degree that about 90% of crushed pieces could pass through a 200-mesh sieve, to obtain powdery dried products. The GABA contents of the powdery dried products were measured, and the results are shown in Table 23. For comparison, the kale juice was processed into a powdery dried product without adding a sodium glutamate solution to the juice. Such a powdery dried product is shown in Table 23 as "non-treated".

TABLE 23

| Duration (hour) | GABA content (mg/100 g) | GABA enriched rate |
|---|---|---|
| Non-treated | 340 | (1) |
| 0.5 | 1870 | 5.5 |
| 1 | 2414 | 7.1 |
| 5 | 2550 | 7.5 |
| 10 | 2822 | 8.3 |

As is found from Table 23, GABA is sufficiently enriched by incubation of 30 minutes or more.

Example 25

To the kale juice obtained in the manner described in Example 21, added was 50 g of commercially available dried sea tangle crushed to such a degree that about 90% of crushed pieces could pass through a 200-mesh sieve. The resultant solution was diluted with water to obtain a glutamic acid solution having a final concentration of 0.1%, and then adjusted to pH 6.0 with citric acid. The solution was stirred for four hours while keeping at 30° C., then freeze-dried, and crushed to such a degree that about 90% of crushed pieces could pass through a 200-mesh sieve, to obtain a powdery dried product. The GABA content of the powdery dried product was measured, and the results are shown in Table 24. For comparison, the kale juice was processed into a powdery dried product without adding dried sea tangle to the juice. Such a powdery dried product is shown in Table 24 as "non-treated".

TABLE 24

| Food material | GABA content (mg/100 g) | GABA enriched rate |
|---|---|---|
| Non-treated | 340 | (1) |
| Dried sea tangle | 442 | 1.3 |

From Table 24, it is found that GABA can also be enriched by using a glutamic acid-containing food material.

Example 26

Juice was obtained from leaves of cruciferous plants, i.e., kale, cabbage, and broccoli in the manner described in Example 21. To the juice, an appropriate amount of citric acid was added to adjust the pH to 5.0, and then a 30 wt. % sodium glutamate solution was added so that the final concentration of the sodium glutamate was 3%. The resultant solutions were stirred for five hours while keeping at 30° C., then freeze-dried, and crushed to such a degree that about 90% of crushed pieces could pass through a 200-mesh sieve, to obtain powdery dried products. The GABA contents of the powdery dried products were measured, and the results are shown in Table 25 below. For comparison, the juices of kale, cabbage, and broccoli were processed into powdery dried products without adding sodium glutamate to the juices. Such powdery dried products are shown in Table 25 as "non-treated".

TABLE 25

| Plant | GABA content (mg/100 g) | | GABA enriched rate |
|---|---|---|---|
| | Non-treated | After enrichment | |
| Kale | 340 | 2488 | 7.2 |
| Cabbage | 78 | 429 | 5.5 |
| Broccoli | 27 | 248 | 9.2 |

As is found from Table 25, the GABA enrichment according to the present invention is effective for not only kale but also other cruciferous plants, i.e., cabbage and broccoli.

What is claimed is:

1. A food, beverage, or medicine material containing at least one substance selected from the group consisting of a cruciferous plant, cut pieces of the plant, or the juice of the plant or of the cut pieces, wherein the substance is subjected to γ-aminobutyric acid enrichment and blanched, and contains γ-aminobutyric acid enrichment in an amount of 50 mg/100 g or more, wherein the γ-aminobutyric acid enrichment includes at least one treatment selected from the group consisting of anaerobic treatment, 25 to 50° C. thermal retention treatment, and glutamic acid treatment, and wherein the cruciferous plant is selected from the group consisting of kale and cabbage.

* * * * *

UNITED STATES PATENT AND TRADEMARK OFFICE
CERTIFICATE OF CORRECTION

PATENT NO. : 6,632,458 B1
DATED : October 14, 2003
INVENTOR(S) : Toshimitsu Hattori et al.

It is certified that error appears in the above-identified patent and that said Letters Patent is hereby corrected as shown below:

Column 6,
Line 41, "a re" should read -- are --.

Column 9,
Line 66, "abovedescribed" should read -- above-described --.

Column 10,
Line 50, "b e" should read -- be --.

Column 13,
Line 43, "510 mg/100 g" should read -- 50 mg/100 g --.

Column 14,
Line 7, "150 mg/100 g" should read -- 50 mg/100 g --.

Column 15,
Line 17, "land" should read -- and --.

Column 21,
Lines 33-34, "67 g/100 g" should read -- 67 mg/100 g --.

Signed and Sealed this

Sixteenth Day of March, 2004

JON W. DUDAS
*Acting Director of the United States Patent and Trademark Office*